(12) United States Patent
Hoffman et al.

(10) Patent No.: US 6,340,667 B1
(45) Date of Patent: *Jan. 22, 2002

(54) REPTILIAN-DERIVED PEPTIDES FOR THE TREATMENT OF MICROBIAL INFECTIONS

(75) Inventors: Brian F. Hoffman, Key Biscayne, FL (US); Ofer Binah, Kiryat Tivan (IL)

(73) Assignee: Theragem, Inc., Old Tappan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/353,719

(22) Filed: Jul. 14, 1999

Related U.S. Application Data

(63) Continuation of application No. PCT/US98/16659, filed on Aug. 10, 1998.
(60) Provisional application No. 60/061,341, filed on Oct. 8, 1997.

(51) Int. Cl.[7] .......................... A61K 31/74; A61K 35/14; A61K 38/00
(52) U.S. Cl. .................................. 514/2; 514/6; 514/12; 514/21; 530/324; 530/380; 530/385; 530/386; 530/827; 530/829; 424/78.07; 424/529; 424/530
(58) Field of Search ............................ 514/2, 6, 12, 21; 530/324, 380, 385, 386, 827, 829; 424/78.07, 529, 530

(56) References Cited

U.S. PATENT DOCUMENTS

| | | | | |
|---|---|---|---|---|
| 5,239,061 A | * | 8/1993 | Fronticelli et al. | 530/385 |
| 5,370,869 A | * | 12/1994 | Shanbrom | 424/78.22 |
| 5,380,664 A | | 1/1995 | Carver et al. | 436/10 |

FOREIGN PATENT DOCUMENTS

| | | |
|---|---|---|
| JP | 05305126 | 11/1993 |
| WO | 93/08831 | 5/1993 |

OTHER PUBLICATIONS

Ivanov, V.T. et al., Pure & Appl. Chem., 70(1); 67–64, 1988 (Exhibit 5).
Fruitier, I. et al., FEBS Letters, 447:81–86, 1999. (Exhibit 6).
Ivanov, V.T. et al., Biopoly, 43:171–188, 1997. (Exhibit 7).
Karelin, A.A. et al., FEBS Letters, 428:7–12, 1998. (Exhibit 8).
Blishchenko, E.Y. et al., Biochem and Biophys. Res. Comm., 224:721–727, 1996. (Exhibit 9).
Blishchenko, E.Y. et al., Peptides, 18(1):79–85, 1997. (Exhibit 10).
Yatskin, O.N. et al., FEBS Letters, 428:286–290, 1988. (Exhibit 11).
Hobson, D. et al., J. of Exp. Med. 107(2):167–183 (1958). (Exhibit 12).
Wood, D.C. et al., Laborat. Invest., 7(1): 1–8 (1958). (Exhibit 13).
Karelin, A.A., et al., Peptides, 16(4):693–7 (1995). (Exhibit 14).
Nicolas, P. et al., Annu. Rev. Microbiol., 49:277–304, 1995.
Perutz, M.F. et al., Nature, 291:682684, Jun. 25, 1981.
European Search Report for PCT/US98/16659 dated Oct. 23, 1998.

* cited by examiner

Primary Examiner—Christopher S. F. Low
Assistant Examiner—Abdel A. Mohamed
(74) Attorney, Agent, or Firm—Darby & Darby

(57) ABSTRACT

The present invention provides compositions useful as antimicrobial agents which include reptilian hemoglobin, the α and β chains of hemoglobin free of heme, fragments of said proteins or polypeptide fragments thereof and combinations thereof. The compositions exert antimicrobial activity against both bacteria and fungi that is comparable to known antimicrobial peptides from human neutrophils, cathepsin G and azurocidin. Sensitive organisms include Gram-negative bacteria such as *Escherichia coli* and *Pseudomonas aerioginosa*, and the fungus *Candida albicans*. Methods for preparing the compositions also are provided.

25 Claims, 10 Drawing Sheets

Alligator hemoglobin against *Escherichia coli*

Alligator hemoglobin against *Pseudomonas aeruginosa*

Protein concentration (ug/ml)

Alligator alpha chain against *Candida albicans*

Protein concentration (ug/ml)

Alligator alpha chain against *Escherichia coli*

Alligator alpha chain against *Pseudomonas aeruginosa*

Protein concentration (ug/ml)

Alligator beta chains against *Candida albicans*

Protein concentration (ug/ml)

Alligator beta chains against *Escherichia coli*

Alligator beta chains against *Pseudomonas aeruginosa*

Plot of C4-reverse phase HPLC analysis of alligator hemoglobin chains

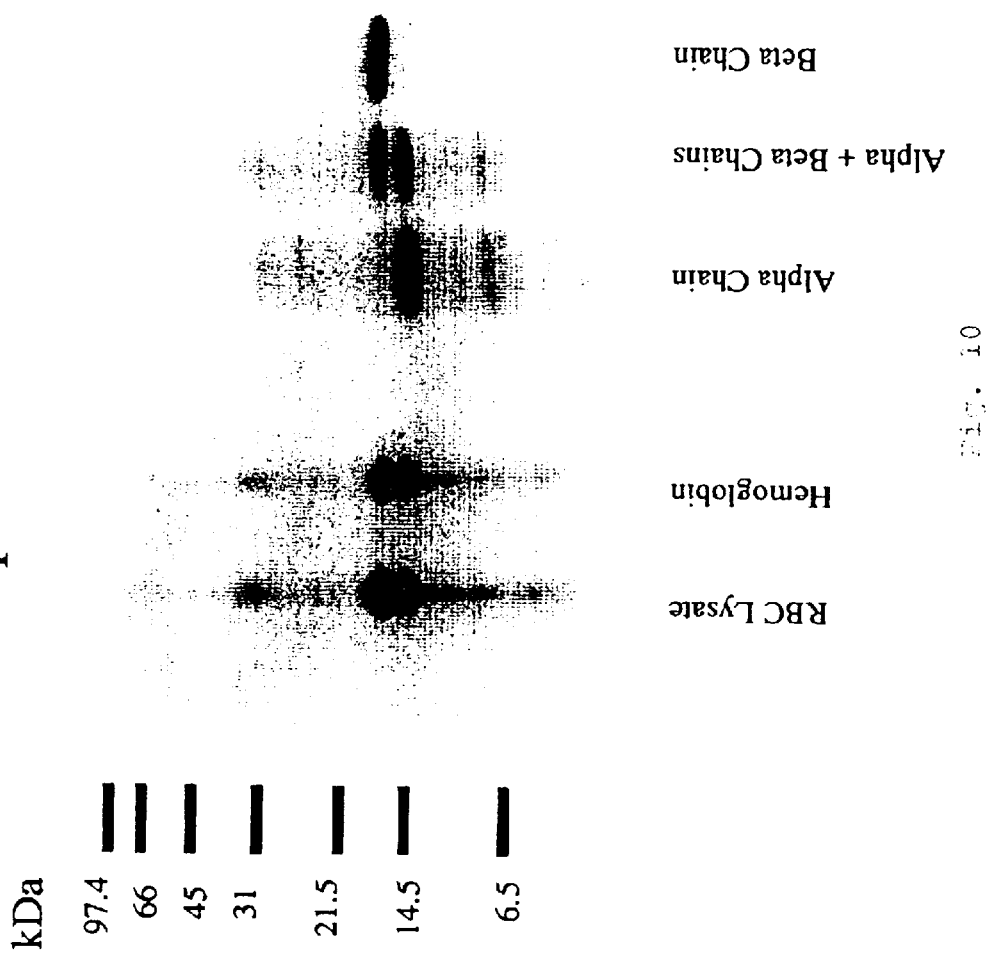

US 6,340,667 B1

REPTILIAN-DERIVED PEPTIDES FOR THE TREATMENT OF MICROBIAL INFECTIONS

This is a continuation of application Ser. No. PCT/US98/16659, filed Aug. 10, 1998, which claims priority of U.S. Provisional Application No. 60/061,341, filed Oct. 8, 1997. Each of these prior applications is hereby incorporated herein by reference, in its entirety.

FIELD OF THE INVENTION

The present invention relates to a method for treating microbial infections of mammals, including humans and other primates; a method for killing bacteria and fungi; and a method for treating material subject to microbial contamination by administration of an effective antimicrobial amount of reptilian hemoglobin, or of the α or β chains of this molecule, free of heme, fragments therefrom and combinations thereof. The invention also relates to compositions comprising such proteins, polypeptides or fragments.

BACKGROUND OF THE INVENTION

Antibacterial peptides from natural sources have a long history. In 1939 Dubos demonstrated that a soil bacillus, subsequently identified as *B. brevis*, produced substances that could prevent pneumococcal infections in mice. Subsequently, Hotchkiss and Dubos purified two substances composed of amino acids and one of these, gramicidin, became available as a therapeutic agent. Subsequent studies on antimicrobial peptides have identified many active agents (1). (Within this application several publications are referenced by Arabic numerals within parentheses. Full citations for these references, listed in sequence, may be found at the end of the specification. All of these references and any additional references cited within this application are herein incorporated by reference in their entirety.)

Many bacteria produce antimicrobial peptides (bacteriocins) and proteins; those released from Gram-negative bacteria are the more potent and have the wider spectrum of activity (2). The defensins are small antimicrobial peptides found in neutrophils, non-human macrophages and Paneth cells (3). Amphibian skin is a rich source of antimicrobial peptides, one of these, magainin, isolated from *Xenopus laevis*, currently is undergoing clinical trial (4,5). Plants form a variety of gene-encoded antimicrobial peptides including the phytoalexins, the PR proteins and the AMPs (6,7). Insects have been shown to synthesize bacteriocidal peptides and proteins such as cecropin obtained from the moth Cecropia (8,9,10) and the sarcotoxins obtained from the larvae of the flesh fly *Sarcocphaga perigrina* (11). The hemocytes of the horse-shoc crab Limulus are the source of the tachyplesins and squalamine, an aminosteroid with antimicrobial activity, has been isolated from the shark, *Squalus acanthias* (12).

Thus, many antimicrobial substances lie within the families of "natural" antibiotics such as the cecropins, magainins, defensins, serprocidins and others. These substances are widely distributed in nature and provide an innate defense mechanism against infection in species ranging from insects to amphibians to mammals. Generally these substances are stored in cells, to be induced and secreted within the animal when challenged. Many act by disrupting the bacterial cell membrane selectively; many would be toxic to host cells as well, were they not sequestered (13). A number of these compounds have been proposed as being useful as antimicrobial agents (14,15).

Hemoglobin (MW=64,500) consists of four polypeptide chains and four heme prosthetic groups in which the iron atoms are in the ferrous state. The protein, called globin, consists of two α chains and two β chains. In the alligator *Alligator mississippiensis*, the α chain contains 141 amino acid residues and the β chain contains 146 residues. The amino acid sequence of the α (SEQ ID NO:2) and β (SEQ ID NO:1) chains of alligator hemoglobin, is a follows:

(SEQ ID NO: 2)
```
α chain
1               15 16              30 31              45
VLSMEDKSNVKAIWG    KASGHLEEYGAEALE    RMFCAYPQTKIYFPH 46              60 61              75 76              90
FDMSHNSAQIRAHGK    KVFSALHEAVNHIDD    LPGALCRLSELHAHS 91             105 106            120 121             135
LRVDPVNFKFLAHCV    LVVFAIHHPSALSPE    IHASLDKFLCAVSAV 131    141
LTSKYR
```

(SEQ ID NO: 1)
```
β chain
1               15 16              30 31              45
ASFDAHERKFIVDLW    AKVDVAQCGADALSR    MLIVYPWKRRYFEHF 46              60 61              75 76              90
GKMCNAHDILHNSKV    QEHGKKVLASFGEAV    KHLDNIKGHFANLSK 91             105 106            120 121             135
LHCEKFHVDPENFKL    LGDIIIIVLAAHHPE    DFSVECHAAFQKLVR 136    146
QVAAALAAEYH
```

The structure of heme (ferroprotoporphyrin IX) is well known.

One heme group is bound to each polypeptide chain through a coordination bond between the iron atom and the R group of a histidine residue. The sixth coordination bond of the iron atom is available to bind oxygen. In addition, hemoglobin also transports $H^+$, $CO_2$, and NO. The structure of heme is identical in all animals that have hemoglobin but the sequence of the globin chains varies considerably. In spite of this variation, the configuration of the tetramer is quite similar among species.

The interactions of hemoglobin with oxygen and carbon dioxide depend on the state of the heme and the residues surrounding it, as well as on regulation by heterotrophic ligands including $H^+$, $Cl^-$, $CO_2$, $HCO_3^-$ and 2,3, diphosphoglycerate. These ligands regulate the equilibrium between the high affinity state (the relaxed or R structure), and the low affinity tense state (or T structure). The stereochemistry of hemoglobin has been reviewed extensively (16,17).

The hemoglobin of reptiles, Chelonia (turtles), Crocodilia (crocodilians) and Squamata (snakes and lizards) shows certain unique structural characteristics (18). In several species the hemoglobin tetramers have been found to form disulfide bridges with each other (19), although this may be largely an in vitro artifact. Also, high levels of methemoglobin (iron in the ferric state) have been found in spite of adequate levels of methemoglobin reductase (20). In most reptiles ATP is the primary regulator of oxygen affinity (21,22). In contrast, hemoglobin in crocodiles and alligators is unique (23), in that it is not responsive to organic phosphates but rather is regulated primarily by the bicarbonate ion which induces a decrease in oxygen affinity. The loss of sensitivity to phosphates apparently is caused by replacement of Pro or Ser for His at β NA2 and replacement by Ala for His at β H21. Also, the N-terminus of the chain of the hemoglobin from *Alligator mississippiensis* is blocked by an acetyl group (24,25,26). This alteration at the N-terminus permits hydrogen bonding with bicarbonate ions on the chains (25,26).

Mammalian hemoglobin-based compositions have been developed for administration as blood substitutes. (27,28) These include chemically modified hemoglobin which contains the oxygen-carrying heme group required for proper oxygen transport. While such modified hemoglobin-based compounds have been administered as blood substitutes, administration of unmodified hemoglobin, its heme free subunits or fragments or synthetic peptides therefrom has not previously been disclosed for this purpose or for other therapeutic uses. Indeed, the heme free α and β subunits would not be utilized for the purpose of providing blood substitutes, as they are incapable of binding oxygen.

SUMMARY OF THE INVENTION

The present invention provides a method for killing bacteria or fungi comprising contacting the bacteria or fungi with an antimicrobially effective amount of reptilian hemoglobin protein, hemoglobin protein fragment or polypeptide fragments thereof selected from the group consisting of intact hemoglobin, heme-free hemoglobin α chain, heme-free hemoglobin β chain, fragments of said proteins or polypeptide fragments thereof and combinations thereof.

The invention also provides a method for treating a subject having a bacterial or fungal infection comprising administering an antimicrobially effective amount of said protein, polypeptides and/or fragment compositions, to a method for treating material subject to bacterial or fungal contamination comprising applying to or admixing with said material an antimicrobially effective amount of said compositions, and to the use of said compositions for antimicrobial treatment of bacteria or fungi.

The invention additionally provides a pharmaceutical dosage form comprising an antimicrobially effective amount of said protein, polypeptide and/or fragment compositions and pharmaceutically acceptable carriers.

BRIEF DESCRIPTION OF THE DRAWINGS

FIG. 10: Tris-tricine-SDS-PAGE analysis of alligator hemoglobin showing coomassie blue staining of both the alpha and beta chains at 14.5 kDa.

DETAILED DESCRIPTION OF THE INVENTION

The subject of the invention is the antimicrobial activity of reptilian hemoglobin, its heme-free α and β chains, fragments therefrom and combinations thereof, and compositions comprising such peptides and fragments. Therapeutic applications for these substances include use as broad spectrum topical and systemic antibacterial and antifungal agents, and agents exhibiting synergism with standard antibiotics.

This invention further provides compositions of matter and methods for treating microbial infections. More particularly, the compositions of this invention comprise hemoglobin or its α or β chains, the latter without heme, derived from reptilian red blood cells.

Further, these compositions also include fragments therefrom or combinations thereof. Bacteria against which the compositions have bactericidal activity include Gram-negative bacteria. Examples of such Gram-negative bacteria are *Escherichia coli* and *Pseudomonas aeruginosa*. Additionally, the compositions act as antimicrobial agents against fungi including yeast. In one embodiment of the invention, the yeast is *Candida albicans*.

Figure 1:
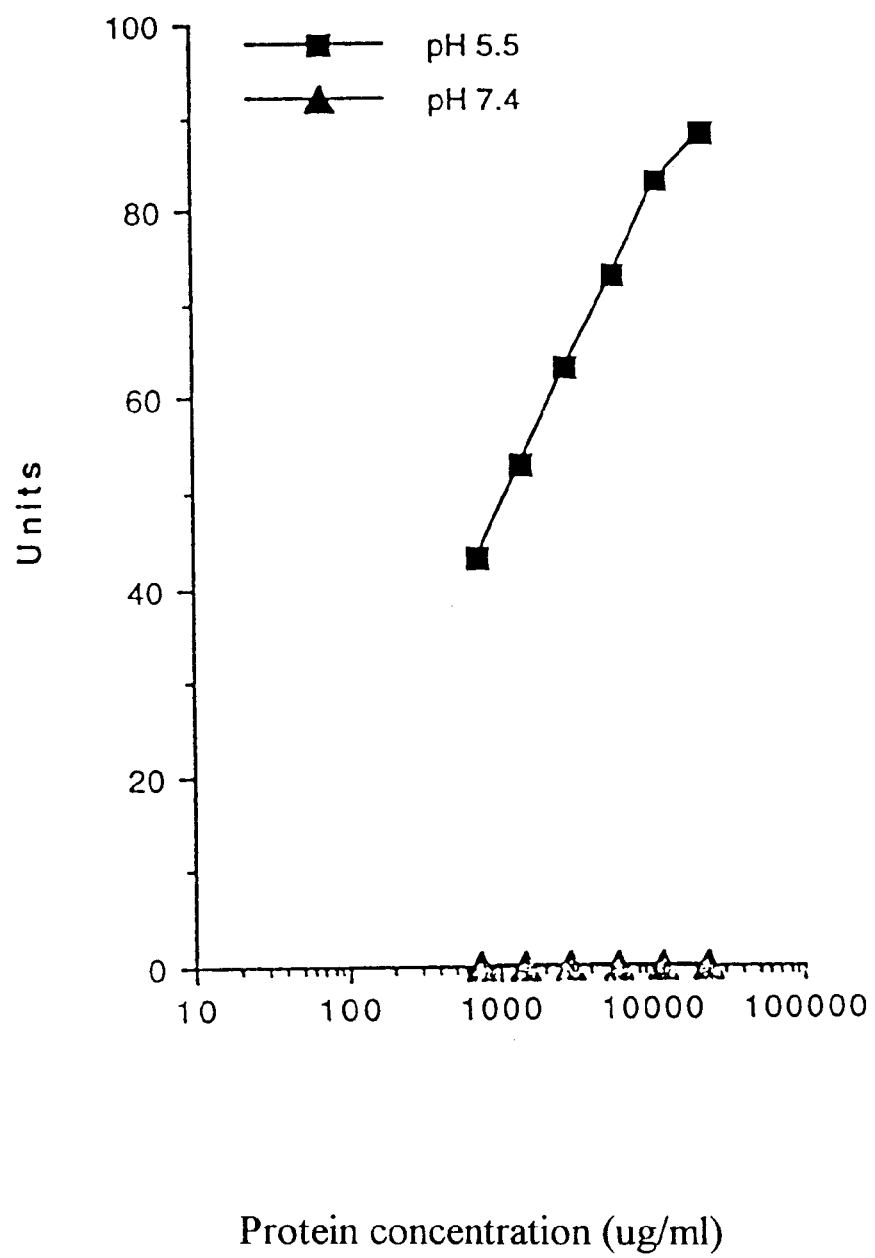
FIG. 1: Activity of hemoglobin against *Escherichia coli* at pH 5.5 and 7.4.
Figure 2:
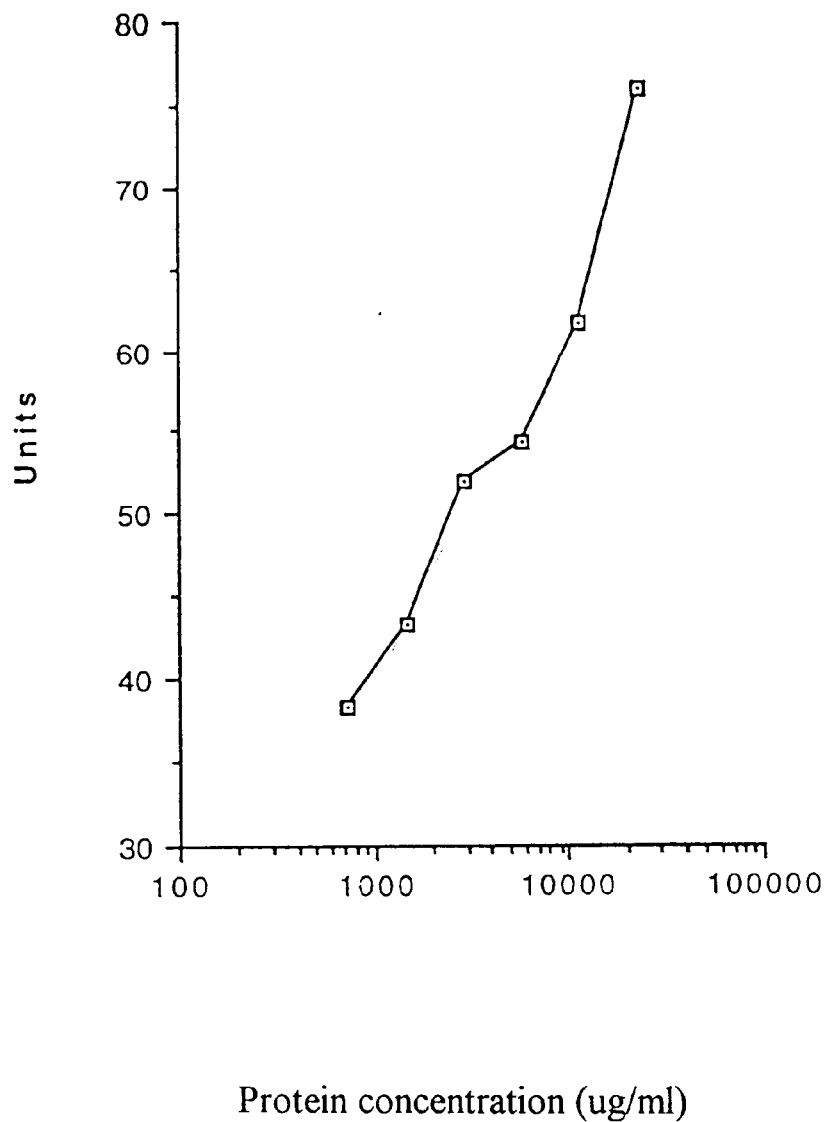
FIG. 2: Activity of hemoglobin against *Pseudomonas aeruginosa* at pH 5.5.
Figure 3:
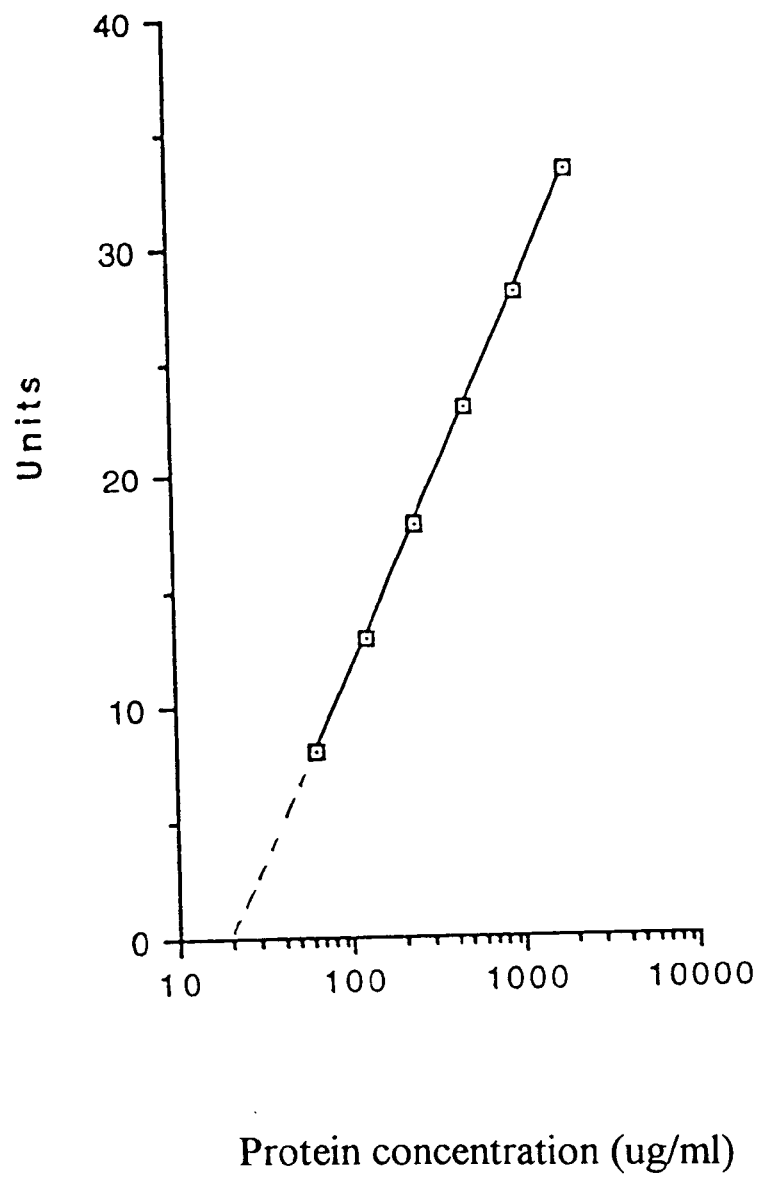
FIG. 3: Activity of alpha chain against *Candida albicans* at pH 5.5.

Alligator hemoglobin exerts antimicrobial activity at pH 5.5 against fungi, such as *Candida albicans* and Gram-negative bacteria, such as *Escherichia coli* and *Pseudomonas aeruginosa*. (FIGS. 1 through 3.)

Figure 4:
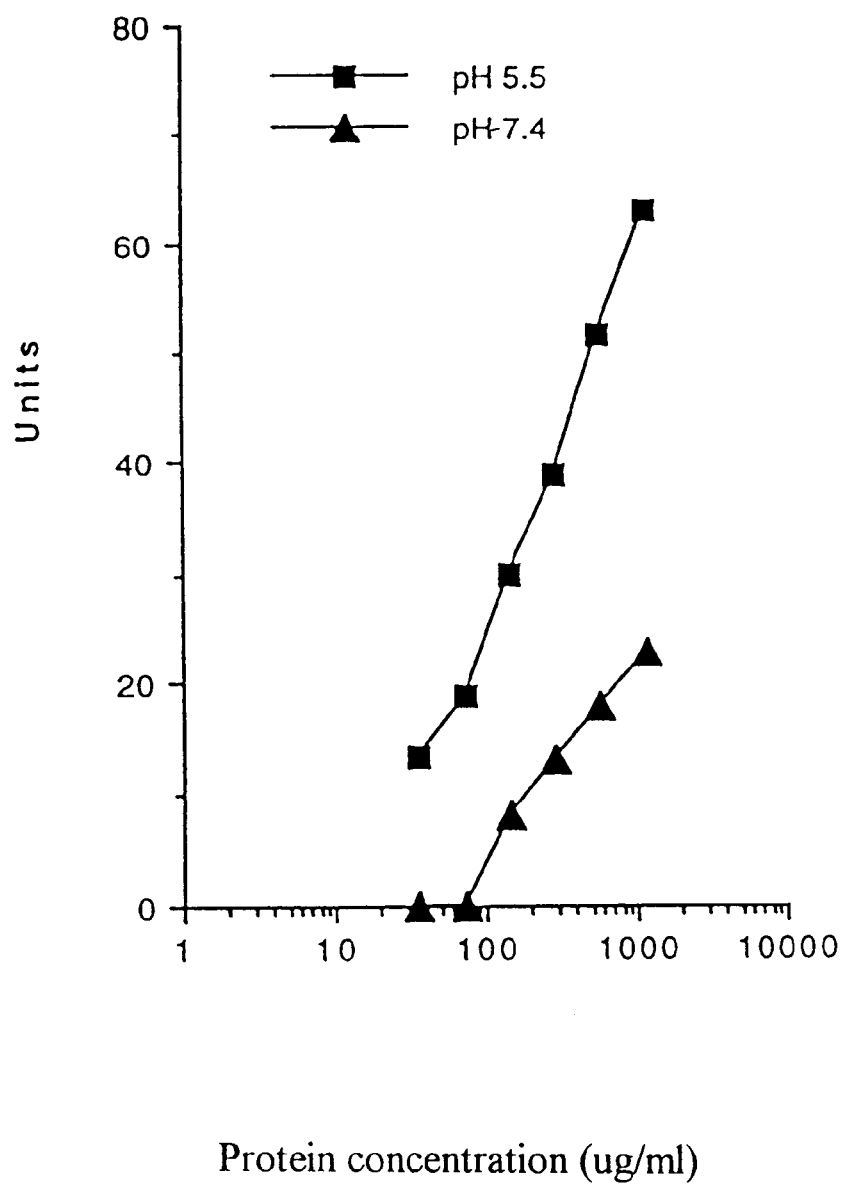
FIG. 4: Activity of alpha chain against *Escherichia coli* at pH 7.4.
Figure 5:
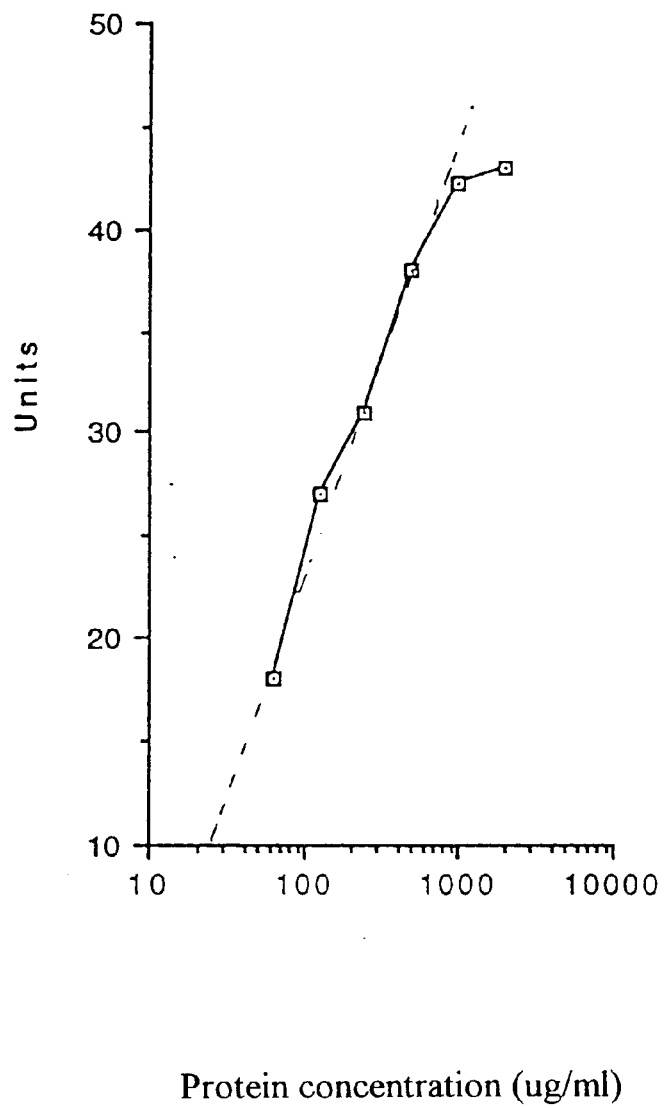
FIG. 5: Activity of alpha chain against *Pseudomonas aeruginosa* at pH 5.5.
Figure 6:
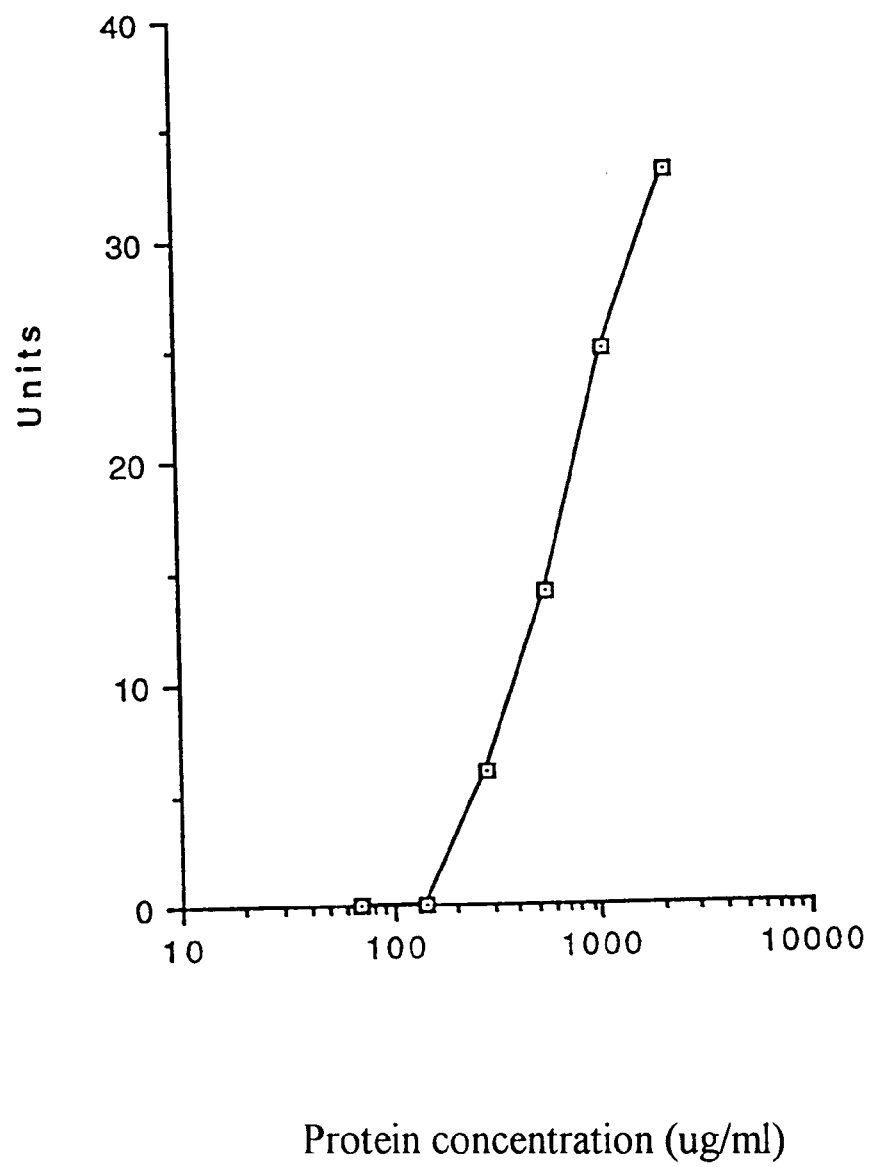
FIG. 6: Activity of beta chain against *Candida albicans* at pH 5.5.
Figure 7:
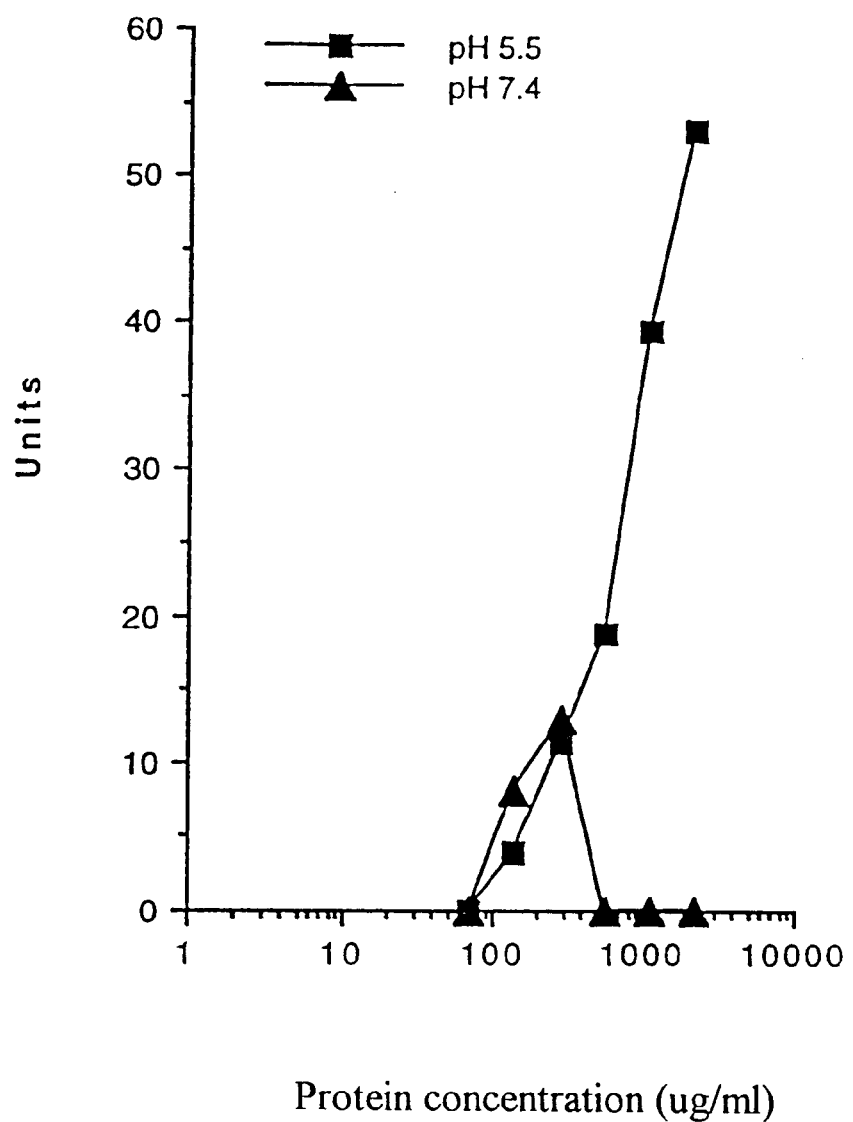
FIG. 7: Activity of beta chain against *Escherichia coli* at pH 5.5.
Figure 8:
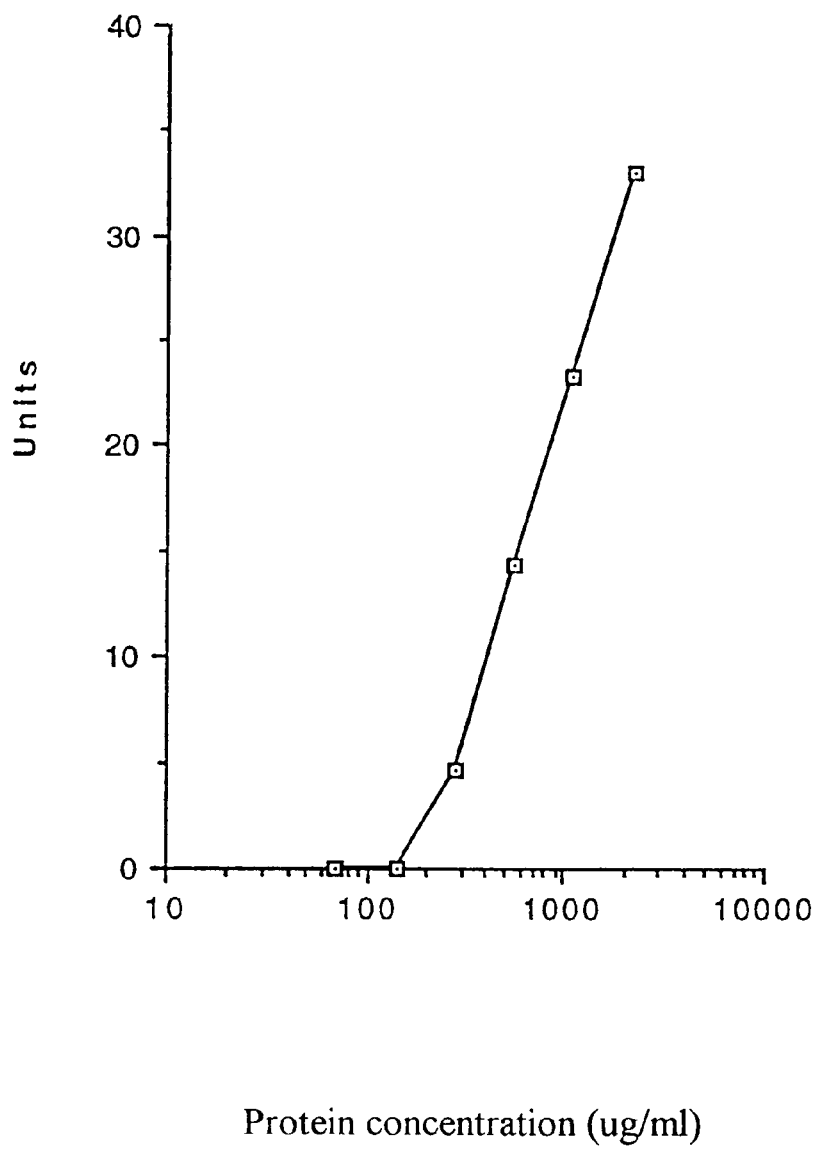
FIG. 8: Activity of beta chain against *Pseudomonas aeruginosa* at pH 5.5.

Similar antimicrobial activity is exhibited at pH 5.5 for the heme-free α and β chains of alligator hemoglobin. (FIGS. 4 to 6 for heme-free α chain; and FIGS. 7 to for the heme-free β chain.)

Hemoglobin from the garter snake is also active.

Although any mechanism proposed to account for the action of these peptides should not be considered limiting, it may be that the antimicrobial activity is contributed from the unique structure of the peptides which may form pores inside the membrane of the microorganisms. Because of similarities in the structure and configuration of hemoglobins from a variety of reptiles, it is likely that hemoglobin, its α and β chains and fragments thereof obtained from sources other than alligator and snake will exert significant antimicrobial activity. The invention thus also encompasses hemoglobin tetramers and their constituent heme-free monomers from other reptiles.

The compositions of the invention may be used therapeutically, as preservatives or as disinfectants. This invention thus comprises a method for antimicrobially treating bacteria or fungi. This method comprises exposing the bacteria or fungi to an antimicrobially effective amount of one of the compositions described herein according to any and each of the technologies described herein. When carrying out the method, the compositions are typically dissolved in an appropriate buffer. Examples of appropriate buffers are known in the art and include phosphate buffer (for fungi) or phosphate buffered saline at suitable values of pH.

The invention further provides a pharmaceutical composition useful for treating bacterial or fungal infections in a human or other mammalian subject by topical or systemic application. This pharmaceutical composition comprises an antimicrobially effective amount of one of the compositions of the invention and a pharmaceutically acceptable carrier. Suitable pharmaceutically acceptable carriers for topical, oral or systemic use are known in the art and are disclosed in the Pharmacopeia of the United States, The National Formulary and Pharmaceutical Science ($8^{th}$ Edition, Chapters 83, 84 and 89).

Depending on the specific application contemplated, the pharmaceutical composition provided by the present invention may be formulated as a solution, suspension, parenteral preparation, ointment, cream, lotion, spray, powder, tablet or capsule which is dosed, applied or admixed as appropriate. Parenteral preparations may include a vehicle such as specially distilled pyrogen-free water, phosphate buffer, or normal saline. Ointments, creams, lotions and sprays may include a carrier such as vegetable or mineral oil, white petrolatum, or a high molecular weight alcohol, i.e., possessing greater than 12 carbon atoms. Tablets or capsules may include diluents, e.g., lactose, binders, lubricants, e.g., stearic acid, and a disintegration aid, e.g., corn starch.

Each of the compositions of this invention may be combined with other antibiotics or antimicrobial agents, aritiprotozoal agents, wound-healing agents and the like to enhance their activity or therapeutic spectrum.

Also provided is a method for treating a human or other mammalian subject having a bacterial or fungal infection which comprises administering to the subject an antimicrobially effective amount of one of the pharmaceutical compositions of the present invention. The compositions can be administered to the subject by, for example, intravenous injection, intraperitoneal injection, orally, or in the form of an aerosol spray composition. Lipid vesicles or lipid emulsion preparations containing the peptides of the invention can also be used for administering the compositions. Specific modes of administration will depend on the pathogen to be targeted. The selection of the specific route of administration and the dose regimen is to be adjusted or titrated by the clinician according to methods known to said clinician in order to obtain the optimal clinical response. The amount to be administered is that amount which is antimicrobially effective. The dosage administered will also depend on the characteristics of the subject being treated, e.g., the particular mammal treated, age, weight, health, types of concurrent treatment, if any, frequency of treatments, and therapeutic ratio. In the case of the treatment of human subjects, the antimicrobially effective amount will typically be in the range of from about 0.5 to 50 mg/kg body weight, and in the range of from about 0.5–5.0 mg/ml per dose.

Also provided is a method for using such peptides to prevent microbial contamination of food, i.e. as a preservative or to eliminate potential pathogens. For example, shell fish, meats and poultry products routinely habor the growth of enteric pathogens. Such pathogens can be eliminated by treatment with an antimocrobially effective amount of the peptide compositions of the invention. Food crops, such as fruits and vegetables could also be treated to eliminate post harvest spoilage. The peptides could be administered topically or through transgenic expression of a recombinant peptide of the invention. In the instance where the material to be preserved is mixed with the composition of the invention, an antimicrobially effective amount of the selected peptide is added by a simple blending method. The antimicrobially effective amount will typically be in the range of from about 1500 $\mu$g to 50 mg/kg of treated material. In the instance where the compositions are administered topically, the antimicrobially effective amount will typically be in the range of from about 0.1–1.0 mg/cm$^2$.

Additionally, the peptides of the invention can be used as disinfectant agents to sterilize or maintain microbe-free products. Such products can include baby wipes, diapers, bandages, towelettes, make-up products, eyewash and contact lens solutions. The compositions of the invention may be administered to such products topically, in appropriate buffer or in liposome compositions. The antimicrobially effective amount to be administered will typically be in the range of from about about 1500 $\mu$g to 50 mg/kg of treated material.

The following examples are intended to illustrate but not limit the present invention.

EXAMPLES

Methods and Preparations
Isolation of Reptilian Hemoglobin

Hemoglobin was isolated according to the following protocol. Venous blood of *Alligator mississippiensis* is withdrawn from the sagittal sinus into a syringe containing a concentration of heparin sufficient to prevent clotting. Blood (stored on ice) is equilibrated to room temperature and distributed in 2 polypropylene tubes (20 ml each) and gently mixed with an equal volume of 6% dextran. The suspension is left to stand until the red cells have settled, at room temperature. This takes approximately 2 hrs. To promote better aggregation, approximately 1% dextran is added to each tube (4% dextran final concentration). Centrifugation at 1000 g is used to separate red blood cell (pellet) from white blood cells/serum (supernatant). The red blood cell pellet is then washed 1× in PBS and stored at −20° C.

Hemoglobin from the garter snake *Thamnophis sirtalis* was purchased from Sigma Chemicals.

Purification of Hemoplobin (29)

The frozen red blood cell pellet was thawed (7.5 mL) and mixed with 2.5 volumes of chilled deionized water. The resulting solution was hand shaken and kept on ice for 15 min. The lysate was centrifuged at 20,000×g for 1 hr. The upper ⅔ of this solution (20 mL) was removed and passed through a mixed-bed ion-exchange column (15 mL, Bio-Rex RG501-X8, Bio-Rad). The effluent was then passed through a 0.22 $\mu$m filter (Millipore) by gravity. The filtrate was diluted with an equal volume of 0.1 M Tris-HCL (ph 7.8) to provide crude hemoglobin (Hb).

Separation of α and β Chains from Hemoglobin (30)

Figure 9:
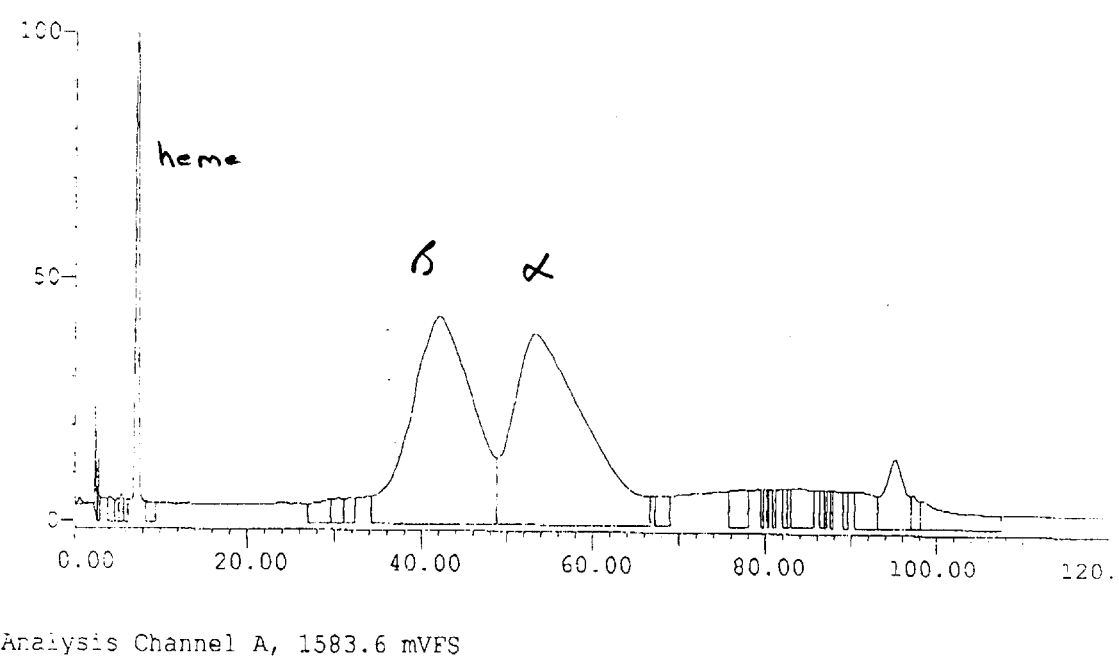
FIG. 9: Plot of C4-reverse phase HPLC analysis of alligator hemoglobin chains showing an early peak representing heme and subsequent broader peaks representing the alpha and beta chains.

Crude Hb (50 $\mu$L) was injected onto a C4 reverse-phase HPLC column (YMC Protein-RP, 150×4.6 mm I.D.) and eluted with water/acetonitrile (mobile phase A; 80% $H_2O$/20% AcCN/0.1 TFA; mobile phase B: 40% $H_2O$/60% AcCN/0.1 TFA). The column was initially washed with 40% mobile phase B for 10 min, after which a linear gradient was run from 45% to 60% of B over 90 min. A second linear gradient from 55% to 95% of B was run over 10 min, after which the column was maintained at 95% B for 15 min. The flow rate of the column was 1 mL/min and eluted material was detected at 210 nm. The eluted volume was collected in 4 mL fractions which were concentrated under vacuum. The heme eluted as a sharp peak at 7.15 min, while the α and β subunits eluted as broad peaks centered at 54 min and 42 min, respectively (FIG. 9).

Tris/tricine-SDS-PAGE Analysis of Hemoglobin and its α and β Chains (31)

Aliquots (20 $\mu$L) of Hb and its α and β chains were combined with 6× sample buffer (4 $\mu$L), heated at 95° C. for 5 min and analyzed by SDS-PAGE (16.5% gel) using a tris/tricine buffer system. The bands were visualized by coomassie blue staining (0.1% coomassie blue G-250 in 50% methanol/10% acetic acid) for 1 h, followed by destaining of each gel (5% methanol/7% acetic acid) overnight (FIG. 10).

Measurement of Antimicrobial Activity

Microbes utilized in the described assays were as follows:
  *Pseudomonas aeruginosa* was strain PA01, *Escherichia coli* was strain MC4100 and *Candida albicans* was a clinical isolate from the Presbyterian Hospital.

Antibacterial Activity
A. Plate Assay

The antibacterial activity of purified fractions, hemoglobin or its α and β chains, was tested against bacteria, typified by *Escherichia coli*, maintained on Trypticase Soy Broth (ISB) agar plates. *Escherichia coli* is used as a representative of Gram-negative organisms. A single colony is inoculated into trypticase soy broth and grown to mid-exponential phase ($OD_{600}$=0.75). The cultures are washed and diluted in 10 mM sodium phosphate buffer (NaPB) (p5.5 or 7.4), 150 mM NaCl (PBS) to a final concentration of $2 \times 10^4$ colony forming units (CFU)/ml. Bacteria are incubated for 1 hour at 37° C. with suitable concentrations of hemoglobin or the α or β chains in PBS assay buffer. At the end of the assay, aliquots are diluted 1:10 in PBS and plated on agar plates with 0.8% soft agar to determine bacterial survival after overnight incubation at 37° C. Bactericidal activity is determined by calculating the decrease in colony forming units for bacteria incubated with hemoglobin or its α or β chains as compared to bacteria incubated with buffer alone.

B. Radial Diffusion Assays for Antibiotic Activity Against *Pseudomonas aeruginosa* PA01

A single colony of *Pseudomonas aeruginosa* PA01 is inoculated into trypticase soy broth and grown to mid-exponential phase ($OD_{600}$=0.7). The cultures are washed in NaPB pH 5.5 and dissolved to a final concentration of $5 \times 10^7$ CFU/ml. A 0.2 ml aliquot of this bacterial suspension ($10^7$ CFU) is added to 10 ml of autoclaved and cooled (to 42° C.) NaPB, buffer, 1% w/v of low electroendosmosis type agarose (Sigma). After mixing the bacteria in, the agarose is poured into Lab-Tek square Petri dishes to form a uniform 1 mm thick layer. Wells with a 2.7 mm diameter are punched in and filled with 4.5 ul of control or sample, the plates are incubated for 3 hours at 37° C., and overlaid with 10 ml of sterile agar maintained at 42° C. The overlay agar is 6% (w/v) TSB and 1% w/v Bacto-agar. After incubation for 18–24 hours at 37° C., the diameter of the clear zone surrounding the wells containing an antibacterial agent is measured.

C. Radial Diffusion Assay for Antibiotic Activity Against *Escherichia coli* MC4100

A single colony of *Escherichia coli* MC4100 is inoculated into TSB and grown to mid-exponential phase ($OD_{600-0.7}$). The cultures are washed in NaPB, pH 5.5 and dissolved to a final concentration of $5 \times 10^7$ CFU/ml. A 0.2 ml aliquot of this bacterial suspension ($10^7$ CFU/ml) is added to 10 ml of autoclaved and cooled (to 42° C.) NaPB buffer containing 0.02% Bovine Serum Albumin (BSA) and 0.02% Triton X100, 1% w/v of low electroendosmosis type agarose (Sigma). After mixing the bacteria in, the agarose is poured into Lab-Tek square Petri dishes to form a uniform 1 mm thick layer. Wells with a 2.7 mm diameter are punched in and filled with 4.5 ul of control or sample, the plates are incubated for 3 hours at 37° C., and overlaid with 10 ml of sterile agar maintained at 42° C. The overlay agar is 6% (w/v) TSB and 1% w/v Bacto-agar. After incubation for 18–24 hours at 37° C., the diameter of the clear zone surrounding the wells containing an antibacterial agent is measured.

Antifungal Activity

A. Plate Assay

The antifungal activity of hemoglobin or its α or β chains is tested against a fungus, as typified by *Candida albicans*, maintained on Sabouraud dextrose agar plates. The fungus *Candida albicans* used in these assays is a clinical isolate from Columbia Presbyterian Hospital, N.Y. A single colony is inoculated in Sabouraud dextrose broth and cultured for 16–18 hrs at 37° C. An aliquot of the overnight culture is inoculated in fresh broth and grown for 3 hrs to a density of $7 \times 10^6$/ml as determined with a counting chamber. The fungus culture is diluted to a final concentration of $2 \times 10^4$ CFU/ml in NaPB, pH 5.5 and this suspension is incubated for 3 hrs with hemoglobin or its α or β chains in NaPB, pH 5.5. Aliquots are diluted 1:10 in M63 minimal media and spread onto Sabouraud dextrose agar plates to determine surviving CFU after 20 hrs at 37° C.

B. Radial Diffusion Assay

The fungus is grown for 3 hrs from an overnight culture in Sabouraud dextrose broth, centrifuged at 10,000 g for 10 min, washed twice in NaPB, p5.5, and resuspended in NaPB (pH 5.5) at a final concentration of $4 \times 10^7$/ml. A 0.1 ml aliquot of this fungal suspension ($4 \times 10^6$ CFU) is added to 10 ml of autoclaved and cooled to (42° C.) NaPB, pH 5.5 containing 1% w/v of low electroendosmosis type agarose (Sigma). After mixing the fungus in, the agar is poured into Lab-Tek square Petri dishes to form a uniform 1 mm thick layer. Wells with a 3 mm diameter are punched in and filled with 5 µl of control or sample, the plates are incubated for 3 hrs at 37° C. and overlaid with 10 ml of sterile agar maintained at 42° C. The overlay agar is 2× Sabouraud agar. After incubation of 18–24 hrs at 37° C., the diameter of the clear zone surrounding the wells containing an antifungal agent is measured.

Antimicrobial Activity of Peptides

Measurement of the antimicrobial activity of alligator hemoglobin and its heme-free α and β chains was determined by radial diffusion assay. For the data provided in FIGS. 1–8, the ordinate shows diameter of clear zone expressed in arbitrary units where ten units=1.0 mm (32). Abcissa shows protein concentration in µg/ml. MIC is estimated by linear extrapolation of data points to the x axis.

Measurement of the antimicrobial activity of alligator and garter snake hemoglobin against yeast also was determined by plate assay.

Each radial diffusion assay was performed with 3 experimental runs except where indicated. The radial diffusion assay is reliable and gives consistent results when used with the purified or semipurified compositions of the invention. The assay method was patterned after that of Lee et al (32).

Example 1

Antimicrobial activity for *Alligator mississippiensis* hemoglobin is summarized in Table 1, Example 1 and in FIGS. 1 through 3. The minimum effective concentration (MIC), expressed as ug/ml, at pH 5.5 was as follows: for *Escherichia coli*, 40–50 ug/ml and *Pseudomonas aeruginosa*, 300 ug/ml.

Examples 2 and 3

In addition, antimicrobial activity was exhibited by the α and β chains of the *Alligator mississippiensis* hemoglobin lacking the heme group. This activity is summarized in Table 1, Example 2 and FIGS. 4–6 for the α chain and Table 1, Example 3 and FIGS. 7–8 for the β chain.

TABLE 1

ANTIMICROBIAL ACTIVITY
Radial Diffusion Assays
Alligator Hemoglobin and heme-free α and β Subunits
Minimum Inhibitory Concentration (MIC) in µg/ml

| Microorganism | Hemoglobin Example 1 | α chains Example 2 | β chains Example 3 |
|---|---|---|---|
| Candida albicans | — | 20–30 | 90–150 |
| Escherichia coli | 40–50 | 10–20 | 20–100 |
| Pseudomonas aeruginosa | 300 | 25–100 | 350 |

Lack of effect indicated by (—)

Example 4

Hemoglobin for the alligator, *Alligator mississippiensis*, was active against *Candida albicans* at an $LD_{50}$ concentration ranging from 4–8 μg/ml in a plate assay.

Example 5

Hemoglobin from the garter snake, *Thamnophis sirtalis*, was active against *Candida albicans* at an $LD_{50}$ concentration of 2.5 ug/ml in a plate assay.

The foregoing examples demonstrate experiments performed and contemplated by the present inventors in making and carrying out the invention. It is believed that these examples include a disclosure of techniques which serve to demonstrate the practice of and usefulness of the invention. It will be appreciated by those skilled in the art that various changes may be made in the embodiments and techniques exemplified without departing from the scope of the invention.

REFERENCES

1) Moberg C L, Cohn Z A (eds). 1990. Launching the antibiotic era. Personal accounts of the discovery and use of the first antibiotics. Rockefeller University Press, New York.
2) Sahl E-G. 1994. Gene enclosed antibiotics made in bacteria, in: Antimicrobial Peptides, Wiley, Chichester, pp 27–53.
3) Ganz T. 1994. Biosynthesis of defensins and other antimicrobial peptides, In: Antimicrobial Peptides, Wiley, Chichester, pp 63–37.
4) Zasloff M. 1987. Magainins, a class of antimicrobial peptides from Xenopus skin: isolation, characterization of two active forms and partial cDNA sequence of precursor. *Proc Natl Acad Sci* 84: 5449–5453.
5) Giovanni M G, Poulter L, Gibson B W, Williams D H. 1987. Biosynthesis and degradation of peptide derived from *Xenopus laevis* prohormones. *Biochem J* 243:113–120.
6) Dizon R A, Dey P M, Lamb C J. 1983. Phytoalexins: enzymology and molecular biology. *Adv Enzymol Relat Areas of Mol Biol* 55: 1–135.
7) Stintzi A, Hertz or, Pradad V, et al. 1993. Plant pathogenesis-related proteins and their role in defense against pathogens. *Biochemie* 75: 687–706.
8) Hultmark D, Steiner H, Rasmulson T, Boman H C. 1980. insect immunity: purification and properties of three inducible bacteriocidal proteins from hemolymph of immunized pupae of *Hylorphora cecropia*. *Eur J Biochem* 106: 7–16.
9) Hultmark D. 1993. Immune reactions in Drosphila and other insects; a model for innate immunity. *Trends Genet* 9: 178–183.
10) Steiner H, Hultmark D, Engstrom A, Bennich H, Boman H G. 1981. Sequence and specificity of two antibacterial proteins involved in insect immunity. *Nature* 292: 245–248.
11) Natori S. 1990. Dual functions of insect immunity proteins in defense and development. *Res Immunol.* 141: 938–939.
12) Moore K S, Wohrli S, Roger H, et al. 1993. Squalamine; an aminosteriod antibiotic from the shark. *Proc Natl Acad Sci* 90: 1354–1358.
13) Kreil G. 1994. Antimicrobial peptides from amphibian skin; an overview, in, Antimicrobial Peptides, Ciba Foundations Symposium 186, pp 77–90. John Wiley & Sons, Chichester, N.Y.
14) Jacob L, Zasloff M. 1994. Potential therapeutic applications of magainins and other antimicrobial agents of animal origin, in Antimicrobial Peptides, John Wiley & Sons, Chichester, N.Y.
15) Nicolas P, Mor A. 1995. Peptides as weapons against microorganisms in the chemical defense system of vertebrates. *Ann Rev Microbiol* 49: 277–304.
16) Perutz M F. 1990. Mechanisms regulating the reactions of human hemoglobin with oxygen and carbon monoxide. *Annu Rev Physiol* 52:1–25, 1990.
17) Perutz M F. 1979. Regulation of oxygen affinity of hemoglobin: influence of structure of the globin on the heme. *Annu Rev Biochem* 48:327–386.
18) Bauer C, Forster M, Gros G, Mosca A, Perella M, Rollema H S, Vogel D. 1981. Analysis of bicarbonate binding to crocodilian hemoglobin. *J Biol Chem* 256:8429.
19) Bunn H F, Forgel B G. 1986. *Hemoglobin: Molecular, Genetic and Clinical Aspects*, W B Saunders, Company, Philadelphia.
20) Pough F H. 1980. Blood oxygen transport and delivery in reptiles. *Am Zool* 20:173.
21) Barlett G R. 1980. Phosphate compounds in vertebrate red blood cells. *Am Zool* 20:1103.
22) Isaaks R E, Harkness D R. 1980. Erythrocyte organic phosphates and hemoglobin function in birds, reptiles, and fishes. *Am Zool* 20:115.
23) Terwilliger R C. 1980. Structures of invertebrate hemoglobins. *Am Zool* 20:53.
24) Perutz M F. 1983. Species adaptation in a protein molecule. *Mol Biol Evol* 1:1.
25) Leclerq F, Schnek A B, Braunitzer G, Stangle A, Schrank B. 1981. Direct reciprocal allosteric interaction of oxygen and hydrogen carbonate sequence of the haemoglobins of the Caiman (*Caiman crocodylus*), the Nile crocodile (*Crocodylus niloticus*) and the Mississippi crocodile (*Alligator mississippiensis*). *Hoppe-Seyler's Z Physiol Chem.* 362:1151.
26) Perutz M F, Bauer C, Gros G, Leclerq F, Vandecasserie C, Schnek A G, Braunitzer G, Friday A E, Joysey K A. 1981. Allosteric regulation of crocodilian haemoglobin. *Nature* 291:682.
27) Ritter, S. K. 1998. Passing a Bood Test. *Science/Technology, C&EN* May 18, 1998:37–44.
28) Winslow, R. M. 1995. "Blood Substitutes: 1995 in the Literature" from *Blood Substitutes: Physiological Basis of Efficacy*, Chapter 1. Eds. Winslow, R. M. et al., Birkhäuser, Boston.
29) Christensen S M, Medina P, Winslow R W, Snell S M, Zegna A, Marini M A. 1988. Preparation of human hemoglobin Ao for possible use as a blood substitute. *J Biochem Biophys Method* 17:143–154.
30) Masala B, Manca L. 1994. Detection of globin chains by reversed-phase high-performance liquid chromatography. *Methods in Enzymology* 231:21–44.
31) Schagger H, von Jagow G. 1987. Tricine-sodium dodecyl sulphate-polyacrylamide gel electrophoresis for the separation of proteins in the range from 1 to 100 kDa. *Anal Biochem* 166:368–376.
32) Lee I H, Cho Y, Lehrer R I. 1997. Effects of pH and salinity on the antimicrobial properties of Clavanins. *Infections & Immunity* 65:2898–2903.

What is claimed is:

1. A method for killing bacteria or fungi, wherein said bacteria or fungi are selected from the group consisting of gram-negative bacteria or yeast, comprising contacting the bacteria or fungi with a bacterial of fungal cell killing effective amount of a fragment of reptilian hemoglobin protein, selected from the group consisting of a reptilian heme-free hemoglobin α chain, a reptilian heme-free hemoglobin β chain; said reptilian hemoglobin protein fragment retaining bacterial or fungal killing function, wherein said contacting is for a time and under conditions effective to kill bacteria or fungi.

2. The method according to claim 1, wherein said hemoglobin protein, hemoglobin protein fragment or polypeptide fragments are derived from alligator.

3. The method according to claim 2, wherein the alligator is *Alligator mississippiensis*.

4. The method according to claim 1, wherein the bacteria are Gram-negative bacteria.

5. The method according to claim 4, wherein the Gram-negative bacteria are selected from the group consisting of *Escherichia coli* and *Pseudomonas aeruginosa*.

6. The method according to claim 1, wherein the fungi are *Candida albicans*.

7. The method according to claim 1, wherein the reptile is *Thamnophis sirtalis*.

8. A method for killing bacteria or fungi in a subject wherein said bacteria or fungi are selected from the group consisting of gram-negative bacteria and yeast, which comprises administering to the subject a bacterial or fungal cell killing effective amount of a fragment of reptilian hemoglabin protein, selected from the group consisting of a reptilian heme-free henoglobin α chain, a reptilian heme-free hemoglobin β chain; wherein said reptilian hemoglobin fragment retains bacterial or fungal killing function; and, is administered topically for a time and under conditions effective to kill bacteria of fungi in a subject.

9. The method according to claim 8, wherein said hemoglobin protein, hemoglobin protein fragment or polypeptide fragments are derived from alligator.

10. The method according to claim 9, wherein the alligator is *Alligator mississippiensis*.

11. The method according to claim 8, wherein the bacteria are Gram-negative bacteria.

12. The method according to claim 11, wherein the Gram-negative bacteria are selected from the group consisting of *Escherichia coli* and *Pseudomonas aeruginosa*.

13. The method according to claim 8, wherein the fungi are *Candida albicans*.

14. The method according to claim 8, wherein the reptile is *Thamnophis sirtalis*.

15. A method for treating material subject to bacterial or fungal contamination, wherein said bacteria or fungi are selected from the group consisting of gram-negative bacteria and yeast comprising applying or admixing with said material a bacterial or fungal cell killing effective amount of a gragment of reptilian hemoglobin protein, selected from the group consisting of a reptilian heme-free hemoglobin α chain, a reptilian heme-free hemoglobin β chain; said reptilian hemoglobin protein fragment retaining bacterial or fungal killing function, wherein said applying or admixing is for a time and under conditions effective to treat bacterial or fungi in a material.

16. The method according to claim 15, wherein said hemoglobin protein, hemoglobin protein fragment or polypeptide fragments are derived from alligator.

17. The method according to claim 16, wherein the alligator is *Alligator mississippiensis*.

18. The method according to claim 15, wherein the bacteria are Gram-negative bacteria.

19. The method according to claim 18, wherein the Gram-negative bacteria are selected from the group consisting of *Escherichia coli* and *Pseudomonas aeruginosa*.

20. The method according to claim 15, wherein the fungi are *Candida albicans*.

21. The method according to claim 15, wherein the reptile is *Thamnophis sirtalis*.

22. A pharmaceutical dosage form comprising a bacterial or fungal cell killing effective amount of a fragment of reptilian hemoglobin protein, selected from the group consisting of a reptilian heme-free hemoglobin α chain, a reptilian heme-free hemoglobin β chain; and a pharmaceutically acceptable carrier, wherein said fragment of reptilian hemoglobin protein kills bacteria or fungi.

23. The pharmaceutical dosage form according to claim 22, wherein said hemoglobin protein, hemoglobin protein fragment or polypeptide fragments are derived from alligator.

24. The pharmaceutical dosage form according to claim 23, wherein said alligator is *Alligator mississippiensis*.

25. The pharmaceutical dosage form according to claim 22, wherein said hemoglobin protein, hemoglobin protein fragment or polypeptide fragments are derived from *Thamnophis sirtalis*.

* * * * *

SEQUENCE LISTING

<160> NUMBER OF SEQ ID NOS: 2

<210> SEQ ID NO 1
<211> LENGTH: 146
<212> TYPE: PRT
<213> ORGANISM: Alligator mississippiensis

<400> SEQUENCE: 1

```
Ala Ser Phe Asp Ala His Glu Arg Lys Phe Ile Val Asp Leu Trp Ala
 1               5                  10                  15

Lys Val Asp Val Ala Gln Cys Gly Ala Asp Ala Leu Ser Arg Met Leu
                20                  25                  30

Ile Val Tyr Pro Trp Lys Arg Arg Tyr Phe Glu His Phe Gly Lys Met
            35                  40                  45

Cys Asn Ala His Asp Ile Leu His Asn Ser Lys Val Gln Glu His Gly
50                  55                  60

Lys Lys Val Leu Ala Ser Phe Gly Glu Ala Val Lys His Leu Asp Asn
65                  70                  75                  80

Ile Lys Gly His Phe Ala Asn Leu Ser Lys Leu His Cys Glu Lys Phe
                85                  90                  95

His Val Asp Pro Glu Asn Phe Lys Leu Leu Gly Asp Ile Ile Ile Ile
                100                 105                 110

Val Leu Ala Ala His His Pro Glu Asp Phe Ser Val Glu Cys His Ala
            115                 120                 125

Ala Phe Gln Lys Leu Val Arg Gln Val Ala Ala Leu Ala Ala Glu
        130                 135                 140

Tyr His
145
```

<210> SEQ ID NO 2
<211> LENGTH: 141
<212> TYPE: PRT
<213> ORGANISM: Alligator mississippiensis

<400> SEQUENCE: 2

```
Val Leu Ser Met Glu Asp Lys Ser Asn Val Lys Ala Ile Trp Gly Lys
 1               5                  10                  15

Ala Ser Gly His Leu Glu Glu Tyr Gly Ala Glu Ala Leu Glu Arg Met
                20                  25                  30

Phe Cys Ala Tyr Pro Gln Thr Lys Ile Tyr Phe Pro His Phe Asp Met
            35                  40                  45

Ser His Asn Ser Ala Gln Ile Arg Ala His Gly Lys Lys Val Phe Ser
50                  55                  60

Ala Leu His Glu Ala Val Asn His Ile Asp Asp Leu Pro Gly Ala Leu
65                  70                  75                  80

Cys Arg Leu Ser Glu Leu His Ala His Ser Leu Arg Val Asp Pro Val
                85                  90                  95

Asn Phe Lys Phe Leu Ala His Cys Val Leu Val Val Phe Ala Ile His
                100                 105                 110

His Pro Ser Ala Leu Ser Pro Glu Ile His Ala Ser Leu Asp Lys Phe
            115                 120                 125

Leu Cys Ala Val Ser Ala Val Leu Thr Ser Lys Tyr Arg
        130                 135                 140
```